United States Patent [19]

Descamps et al.

[11] Patent Number: 5,204,469
[45] Date of Patent: Apr. 20, 1993

[54] PROCESS FOR THE PREPARATION OF AN N-PHENYLACETIC DERIVATIVE OF TETRAHYDROTHIENO(3,2-C)PYRIDINE AND ITS CHEMICAL INTERMEDIATE

[75] Inventors: Marcel Descamps, Lhum; Joël Radisson, Toulouse, both of France

[73] Assignee: Sanofi, Paris, France

[21] Appl. No.: 725,650

[22] Filed: Jul. 3, 1991

[30] Foreign Application Priority Data

Jul. 10, 1990 [FR] France .................. 90 08749

[51] Int. Cl.$^5$ .................. C07D 513/04; C07D 333/20
[52] U.S. Cl. ......................... 546/114; 549/77
[58] Field of Search ............ 549/77; 546/114; 514/301

[56] References Cited

U.S. PATENT DOCUMENTS

| | | | |
|---|---|---|---|
| 4,127,580 | 11/1978 | Braye | 546/114 |
| 4,174,448 | 11/1979 | Bousquet et al. | 546/114 |
| 4,529,596 | 7/1985 | Aubert et al. | 546/114 |
| 4,847,265 | 7/1989 | Badorc et al. | 514/301 |
| 4,873,343 | 10/1989 | Radisson et al. | 549/74 |

FOREIGN PATENT DOCUMENTS

| | | | |
|---|---|---|---|
| 0000453 | 1/1979 | European Pat. Off. | 546/114 |
| 0099802 | 2/1984 | European Pat. Off. | 546/114 |
| 0281459 | 9/1988 | European Pat. Off. | 546/114 |
| 0321349 | 6/1989 | European Pat. Off. | 546/114 |
| 0342118 | 11/1989 | European Pat. Off. | 546/114 |

OTHER PUBLICATIONS

F. P. Doyle, et al., *J. Chem. Soc.*, "Derivatives of 6-Amino-penicillanic Acid," pp. 1440-1442 (1962).

T. Sohda et al., *Chem. Pharm. Bull.*, "Studies on Antidiabetic Agents," 30 (10), pp. 3601-3616 (1982).
J. March, "Advanced Organic Chemistry," 3rd Ed., pp. 104-109, John Wiley & Sons, New York (1985).

*Primary Examiner*—Richard L. Raymond
*Assistant Examiner*—M. W. Russell
*Attorney, Agent, or Firm*—Wegner, Cantor, Mueller & Player

[57] ABSTRACT

The invention relates to a process for the preparation of the compound of formula

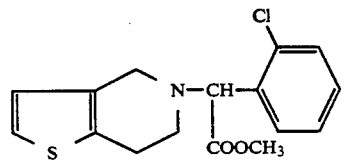

wherein a formylating agent is reacted with the compound of formula

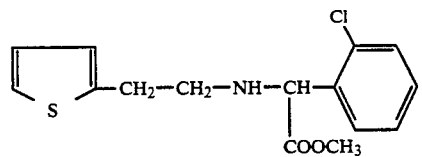

and wherein the compounds obtained are cyclised in the presence of an acid.

7 Claims, No Drawings

PROCESS FOR THE PREPARATION OF AN N-PHENYLACETIC DERIVATIVE OF TETRAHYDROTHIENO(3,2-C)PYRIDINE AND ITS CHEMICAL INTERMEDIATE

The present invention relates to a process for the preparation of racemic methyl alpha-(4,5,6,7-tetrahydro-5-thieno[3,2-c]pyridyl)(2-chlorophenyl)acetate and of its two enantiomers, whose dextrorotatory isomer, clopidogrel, is known for its advantage in therapeutics, especially for its platelet antiaggregating and antithrombotic activities.

A process for the preparation of the racemic mixture by substitution of 4,5,6,7-tetrahydrothieno[3,2-c]pyridine is described in EP-A-99,802, while the isolation of each of the stereoisomers by recrystallisation of the salts with dextrorotatory and laevorotatory camphorsulphonic acids respectively is described in EP-A-0,281,459.

A process of preparation has now been found which makes it possible to obtain, in excellent yields, the racemic mixture but also solely one of the enantiomers. In fact, the process is stereospecific, and there is no racemisation of the asymmetric carbon, whereas it has been found that by applying the process described in the abovementioned EP-A-99,802, that is to say by reacting one of the enantiomers of methyl alpha-(2-chlorophenyl)acetate with 4,5,6,7-tetrahydrothieno[3,2-c]pyridine, a mixture of clopidogrel and of its laevorotatory enantiomer of formula

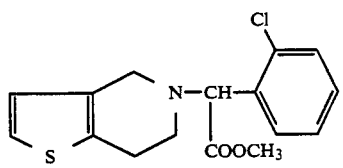

I is obtained.

The process according to the invention consists in reacting a formylating agent with the compound of formula

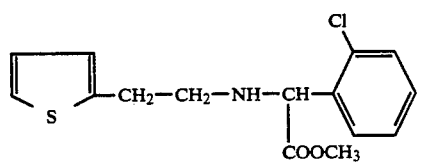

II and in cyclising the intermediate compounds formed in the presence of an acid.

The formylating agents are a) formaldehyde and compounds which are generally known to release it in a reactive form, such as its polymer forms and its hydrate, b) compounds of formula XCH$_2$Y in which X is a halogen atom, a C$_1$-C$_4$ alkoxy group, a C$_1$-C$_4$ alkylthio group or an amino group and Y is a C$_1$-C$_4$ alkoxy, C$_1$-C$_4$ alkylthio, amino, C$_2$-C$_5$ alkoxycarbonyl or phenoxycarbonyl group, and c) the heterocyclic compounds of formula

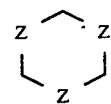

in which Z is O, NH or S, such as s-trioxane.

The two stages of the reaction may be carried out successively, optionally with isolation of the intermediate compounds or simultaneously.

It is considered that a hydroxymethyleneamine or a heterocyclic ring of the trimethylenetriamine type may, in particular, be formed as intermediate compounds, but the invention cannot be limited by these hypotheses.

When the reactions are successive the first stage may be carried out in water or in an alcohol, optionally in the presence of a hydrocarbon solvent such as benzene, toluene or petroleum ether, of a halogenated solvent such as methylene chloride, or of an ether; the cyclisation is then carried out in a polar solvent such as water, an alcohol or dimethylformamide, or in a mixture of these solvents.

The preferred formylating agent is formaldehyde, which may be introduced into the mixture in aqueous solution. The acid may be an organic or inorganic acid, generally strong, such as sulphuric acid or a hydrogen halide acid like hydrochloric acid, or a sulphonic acid like methanesulphonic acid.

When the reactions are carried out simultaneously the reaction medium is a polar solvent such as water or an alcohol, and the inorganic or organic acid is introduced into the medium, preferably in stoichiometric quantity in relation to the compound of formula II employed; in this latter case the acid is a strong acid which may be simply introduced into the medium in the form of its salt with the compound of formula II. It is also possible to employ an acidic solvent such as formic acid or acetic acid, the former used in combination with paraformaldehyde being particularly preferred.

The compound of formula II in racemic form or each of its stereoisomers and their salts, which are necessary for the process, are another aspect of the invention.

They may be prepared by reaction of methyl alpha-amino(2-chlorophenyl)acetate of formula IV with a thienyl derivative of formula III according to the reaction scheme (a):

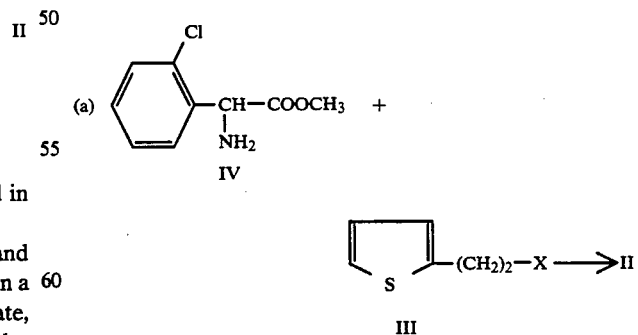

in which X is a halogen atom, especially Br, or a sulphonic group RSO$_2$O- in which R is a C$_1$-C$_4$ alkyl group, or a phenyl group, optionally substituted.

It is preferred to use the more stable p-toluenesulphonic derivative.

The reaction conditions are conventional; the compounds are kept at a temperature of between 50° C. and 100° C. for 10 to 30 hours in an inert solvent, preferably in the presence of a base which neutralises the acid formed. The base employed may be an organic base such as a tertiary amine and more particularly triethylamine, or an inorganic base such as alkali metal carbonates such as $Na_2CO_3$ or $NaHCO_3$, or alkali metal phosphates such as $K_2HPO_4$. Many organic solvents may be employed as reaction medium, including alcohols such as methanol, ketones such as methyl ethyl ketone, ethers such as tetrahydrofuran, nitriles such as acetonitrile, esters such as ethyl acetate, or hydrocarbons, halogenated or not, such as toluene or methylene chloride; however, it has been observed that if it is desired to obtain only one of the enantiomers of the compound II by reacting one of the enantiomers of the compound IV instead of the racemic mixture, the choice of the solvent may be critical, since a partial racemisation takes place in some solvents; esters enable the racemisation to be avoided and it is preferred to use methyl acetate as solvent when the dextrorotatory isomer of the compound IV (hydrochloride: $[\alpha]D/20 = +115°; c=1$, $CH_3OH$) to obtain the dextrorotatory isomer of the compound II ($[\alpha]D/20 = +98°$; $c=0.76$, $CH_3OH$) which, when the process of the invention is applied, gives clopidogrel (dextrorotatory hydrochloride: $[\alpha]D/20 = +65°; c=1$, $CH_3OH$).

It is also possible to prepare the compound of formula II from thienylethylamine, according to the reaction scheme (b):

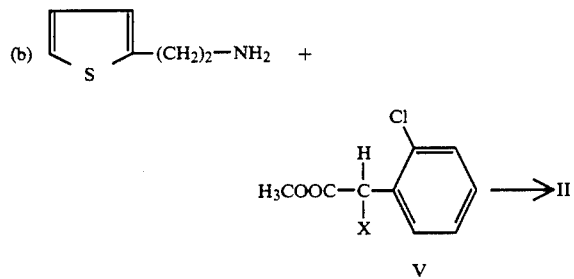

in which X is Cl or Br.

The reaction is carried out in an inert solvent, optionally in the presence of a base, to convert the acid formed into a salt. For example, when X=Br the operation is advantageously carried out in methanol in the presence of an alkali metal carbonate.

The products reacted according to (a) and (b) are known or can be prepared by analogy with known processes.

For example, the preparation of thienylethylamine is described in FR-A-2,608,607, that of the compound III in FR-A-2,300,090, that of the racemic compound V X=Br) in Chem. Pharm. Bull. 30 (10) 3601–3616 (1982); the compound IV may be prepared, for example, by esterification of the racemic amino acid or of each of the enantiomers by reaction with thionyl chloride and methanol at a temperature below 5° C., using a conventional process; the acidic precursor of IV is described in J. Chem. Soc. p. 1440–1444 (1962): these two isomers can be separated conventionally by recrystallisation or by a method involving an enzyme reaction. The two enantiomers of IV can also be separated by recrystallisation with the enantiomers of tartaric acid in the presence or absence of methyl ethyl ketone.

The enantiomers of the compound II are also obtained by recrystallisation of the salt of the racemic compound with an optically active acid such as (+)- or (−)- tartaric acid in isopropanol or (+)- or (−)- 10-camphorsulphonic acid in acetone.

Examples of embodiments of the process according to the invention and examples of preparation of the racemic synthesis intermediates and of their enantiomers are described in what follows. The melting points referred to were determined in a capillary tube. The concentrations of the solutions for measuring rotatory powers are expressed in g/100 ml.

Preparation of methyl
alpha-amino(2-chlorophenyl)acetates (IV)

a) Racemic 330 g of thionyl chloride are introduced into 750 ml of methanol at a temperature below −10° C., followed rapidly by 245 g of alpha-amino(2-chlorophenyl)acetic acid; after stirring for 48 hours at room temperature, the volatile products are removed under reduced pressure; the residue, dissolved in 1,000 ml of methanol, is filtered through active charcoal and the hydrochloride of the required product is precipitated in an excess of isopropyl ether.

After drying, 290 g of the hydrochloride of the racemic aminoester IV, which melts at 198° C., are obtained.

The corresponding aminoester, released from its salt by reaction with $NaHCO_3$ in water and 1,2-dichloroethane, distils between 96° C. and 100° C. at 40 Pa.

b) Dextrorotatory Enantiomer

α-1- 80 g of (+)-10-camphorsulphonic acid are introduced into a solution of 64 g of alpha-amino(2-chlorophenyl)acetic acid in 1.1 l of water under reflux and are left to crystallise for several days at room temperature. The precipitate which has appeared is isolated and the filtrate is concentrated to 150 ml. The precipitate formed is combined with the first one and the whole is recrystallised from water.

This gives 45 g of (+)- camphorsulphonate of (+)-alpha-amino(2-chlorophenyl)acetic acid.
$[\alpha]D/22 = +92°$ (c=1, N HCl).

α-2- esterification:

The base of the salt obtained according to 1 is released by reaction with $NaHCO_3$ and 24.5 g of it are introduced between −20° C. and −8° C. into 75 ml of methanol to which 33 g of thionyl chloride have been added. The mixture is allowed to return to room temperature and is kept stirred for 48 hours before distilling the volatile products under reduced pressure. The residue is dissolved in 100 ml of methanol and this solution is poured into 800 ml of isopropyl ether to precipitate the methyl (+)-alpha-amino(2-chlorophenyl)acetate hydrochloride.

β-45 g of (+)-tartaric acid, 1.2 l of acetonitrile and 25 ml of methyl ethyl ketone at about 60° C. are introduced into a solution of 62 g of the aminoester obtained according to a) in 270 ml of methanol under reflux.

The mixture is kept at about 60° C. for a day and the solid is filtered off at 50° C. and then redissolved in a refluxing mixture of 400 ml of acetonitrile and 100 ml of methanol; the precipitate formed is separated off at 45° C. After drying, 49 g of (+)- tartrate of methyl (+)- alpha-amino(2-chlorophenyl)acetate are obtained [α]D/20= +85.5° (c=1, CH₃OH).

c) Laevorotatory Enantiomer 5.2 g of laevorotatory alpha-amino(2-chlorophenyl)acetic acid [α]$_D$= −115° (c=1, N HCl) are suspended in 100 ml of methanol and a stream of HCl is then bubbled through the mixture, which is being cooled in an ice bath. The mixture is left at a temperature of approximately 5° C. for several days and the solvent is then evaporated off under reduced pressure; 200 ml of methanol are added to the residue and are evaporated off. The required hydrochloride is then precipitated with ethyl ether. This gives 5.32 g of methyl (−)-alpha-amino(2-chlorophenyl)acetate hydrochloride [α]D/20 = −114.5° (c=1, CH₃OH).

Preparation of racemic methyl alpha-chloro(2-chlorophenyl)acetate (V)

93.3 g of 2-chloromandelic acid are mixed with 208 g of PCl₅ and heated slowly to 60° C., at which temperature the exothermic reaction begins; the mixture is then kept for approximately 2 hours between 120° C. and 130° C. until the HCl evolution has ended; the volatile products are then removed under reduced pressure and the residue is dissolved in 200 ml methanol. The mixture is kept at its reflux temperature for 2 hours, the methanol is evaporated off and the residue is then dissolved in CH₂Cl₂. The organic phase is washed with water and the solvent is then evaporated off; the oily residue is distilled under reduced pressure; b.p.=85° C./2000 Pa.

50 g of the required alpha-chloro ester are thus obtained.

EXAMPLE 1

Racemic methyl alpha-(2-thienylethylamino)(2-chlorophenyl)acetate (II - scheme a)

9.6 g of methyl alpha-amino(2-chlorophenyl)acetate are released from its hydrochloride by reaction with 7 g of NaHCO₃ in the presence of 150 ml of CH₂Cl₂ and 50 ml of water.

The amine obtained is dissolved in 50 ml of acetonitrile; 4.8 g of NaHCO₃ and 12 g of 2-thienylethyl paratoluenesulphonate (III, X=CH₃C₆H₄SO₃) are then introduced; the mixture is kept at 80° C. for 22 hours and the volatile products are then evaporated off under reduced pressure. The residue is dissolved in 150 ml of ethyl acetate and 50 ml of water; the organic phase is separated off and 6 g of a concentrated aqueous solution of hydrochloric acid, mixed with 15 g of crushed ice, are introduced into it at about 5° C. The precipitate formed with stirring is filtered off and dried. 9.4 g of the hydrochloride of the compound of formula II are thus obtained. M.p.=175° C.

EXAMPLE 2

Dextrorotatory methyl alpha-(2-thienylethylamino)(2-chlorophenyl)acetate (II - scheme a)

3.46 g of methyl (+)-alpha-amino(2-chlorophenyl)acetate, obtained by reaction of NaHCO₃ in a mixture of water and methylene chloride with the (+) tartrate of methyl (+)-alpha-amino(2-chlorophenyl)acetate, are introduced into 50 ml of methyl acetate together with 4 g of K₂HPO₄ and 6 g of (2-thienyl)ethyl para-toluenesulphonate, and the mixture is kept at about 80° C. for 40 hours. The volatile products are then removed under reduced pressure and the residue is dissolved in a mixture of 75 ml of ethyl acetate and 40 ml of water. The organic phase is separated off and concentrated to one half. 10 g of crushed ice are then introduced into it at about 5° C. with 3 ml of a concentrated aqueous solution of hydrochloric acid.

The precipitate formed is isolated and dried.

3 g of the hydrochloride of the required product are thus obtained.

[α]D/20= +104° (c=1, CH₃OH).

The same product is obtained in a slightly lower yield by replacing the 6 g of (2-thienyl)ethyl paratoluenesulphonate with 4.2 g of 2-(2-bromo)ethylthiophene.

EXAMPLE 3

Dextrorotatory methyl alpha-(2-thienylethylamino)(2-chlorphenyl)acetate by resolution of the racemate a) 175 g of the hydrochloride of the compound II obtained according to Example 1 are dissolved in a mixture of 0.75 l of methylene chloride and 0.25 l of water. 45 g of NaHCO₃ are then added progressively and the organic phase is separated off after stirring and phase separation. After the usual treatments the aminoester is obtained and is dissolved in 850 ml of acetone and 87 g of (+)-10-camphorsulphonic acid are introduced into this solution; after 12 hours at room temperature, the precipitate formed is isolated.

146.5 g of camphorsulphonate are thus obtained. [α]D/22= +51.7° (c=1, CH₃OH).

The camphorsulphonate is suspended in 700 ml of refluxing acetone and 300 ml of methyl ethyl ketone are added to obtain complete solubilisation. The precipitate formed after returning to room temperature is isolated and then treated again by heating with 500 ml of acetone and 300 ml of methyl ethyl ketone to give 95 g of (+)camphosulphonate of the required product.

M.p.=95° C. [α]D/22= +82° (c=1, CH₃OH).

b) 33.5 g of the compound II are introduced into 500 ml of isopropanol with 14.6 g of (+)-tartaric acid; the mixture is heated to 50° C. and then left at room temperature. The precipitate formed is isolated and recrystallised 4 times from isopropanol. The (+)-tartrate of the required dextrorotatory product is finally obtained, which melts at 105° C.

The rotatory power of the amine is [α]D/20= +99.76° (c=1, CH₃OH).

EXAMPLE 4

Laevorotatory methyl alpha-(2-thienylethylamino)(2-chlorophenyl)acetate by resolution of the racemate.

100 g of the hydrochloride of the racemic compound II, followed by 30 g of sodium bicarbonate, are introduced into a mixture of 500 ml of methylene chloride and 200 ml of water. After stirring and phase separation, the organic phase is separated off and the solvent is removed from it by distillation under reduced pressure. The residue is dissolved in 800 ml of acetone and 53.3 g of (−)-10-camphorsulphonic acid are added. The precipitate formed after 12 hours at room temperature is isolated and suspended in 300 ml of acetone. The remaining solid is then recrystallised from a mixture of 600 ml of acetone and 160 ml of methyl ethyl ketone to give 52.5 g of (−)-camphorsulphonate of the required product.

M.p.=95° C. [α]D/22=−82° (C=1, CH₃OH).

EXAMPLE 5

Racemic methyl alpha-(2-thienylethylamino)(2-chlorophenyl)acetate (II - scheme b)

543 g of alpha-bromo(2-chlorophenyl)acetic acid and 30 g of concentrated sulphuric acid are introduced into 300 ml methanol. The mixture is refluxed for 3 hours and, after it has cooled to about 30° C., 230 g of KHCO₃ and 265 g of 2-(2-thienyl)ethylamine are added progressively. The mixture is refluxed for 1 hour 30 min and the solvent is then evaporated off under vacuum. 1 l of water and 1 l of ethyl acetate are poured onto the residue and the organic phase is separated off after stirring and phase separation. 300 ml of ice and 180 ml of concentrated hydrochloric acid are then introduced into it. The precipitated product is filtered off and dried. 641 g of the hydrochloride of the required product, which melts at 175° C., are thus obtained.

EXAMPLE 6

Racemic methyl alpha-(4,5,6,7-tetrahydro-5-thieno[3,2-c]pyridyl)(2-chlorophenyl)acetate (I)

a) 31 g of methyl alpha-(2-thienylethylamino)(2-chlorophenyl)acetate (85%) are dissolved in 50 ml of methylene chloride, and this solution is introduced slowly at T<25° C. into 20 ml of a solution containing 30% (w/w) of formaldehyde in water. The organic phase is separated off and then, after washing with 50 ml of water containing 2% (w/v) of NaCl, it is introduced slowly into 17 ml of a solution of dimethylformamide containing hydrochloric acid (6.5N) at 30° C. After 1 hour's stirring the methylene chloride is evaporated off and 150 ml of water and 150 ml of isopropyl ether are poured into the solution, with potassium carbonate, to obtain a basic pH. The aqueous phase is separated off and 25 ml of a 4.7N aqueous solution of HCl are introduced into the organic phase. The precipitate which has appeared is filtered off and dried to give 23 g of the hydrochloride of the final product, crystallised with one molecule of water. M.p.=130°-140° C.

b) 22 g of racemic methyl alpha-(2-thienylethylamino)(2-chlorophenyl)acetate, released from its hydrochloride, are dissolved in 90 ml of anhydrous formic acid. 3.8 g of powdered paraformaldehyde are then added and the mixture is kept at 50° C. for 20 minutes. The volatile products are then removed under reduced pressure, and 300 ml of water and 250 ml of 1,2-dichloroethane are poured onto the residue. The organic phase is washed with 100 ml of a 5% (w/v) aqueous solution of NaHCO₃ and dried, and the solvent is removed. The residual oil is dissolved in 200 ml of isopropyl ether; 10 ml of concentrated hydrochloric acid and 30 g of ice are introduced into the solution at 5° C. The precipitate formed is separated off and dried. 23 g of the hydrochloride of the required product are thus obtained.

c) 35 g of the hydrochloride of racemic methyl alpha-(2-thienylethylamino)(2-chlorophenyl)acetate are suspended in 150 ml of a 30% (w/w) aqueous solution of formaldehyde. The mixture is kept at 50° C. for 2 hours and then poured, at about 20° C., into 200 ml of methylene chloride. The organic phase is concentrated and the residual oil is dissolved in 120 ml of isopropyl ether in which the hydrochloride is prepared as before; 29.5 g are obtained.

EXAMPLE 7

Dextrorotatorymethyl alpha-(4,5,6,7-tetrahydro-5-thieno[3,2-c]pyridyl)(2-chlorophenyl)acetate (I)

a) 38 g of (+)-camphorsulphonate of methyl (+)-alpha-(2-thienylethylamino)(2-chlorophenyl)acetate are treated with 7 g of NaHCO₃ in a mixture of 200 ml of 1,2-dichloroethane and 70 ml of water. After stirring and separation, the dried organic phase is concentrated.

The residue is dissolved in 90 ml of anhydrous formic acid with 3.8 g of paraformaldehyde, and the mixture is heated to 50° C. for 20 min. The volatile products are removed under reduced pressure and 250 ml of 1,2-dichlorethane and 400 ml of water are poured onto the residue. After stirring and phae separation, the solvent of the isolated organic phase is evaporated off and the residual oil is dissolved in 250 ml of ethyl ether. The hydrochloride of the final product precipitates on addition of HCl-saturated ethyl ether to the solution.

The isolated and dried precipitate weighs 21 g; melts at about 130°-140° C. [α]D/26=+63° (c=1, CH₃OH).

b) A solution of 16 g of (+)-camphorsulphonate of methyl (+)-alpha-(2-thienylethylamino)(2-chlorophenyl)acetate in 50 ml of a 37% (w/w) aqueous solution of formaldehyde is kept at 80° C. for 1 hour 15 minutes. 100 ml of water and 200 ml of methylene chloride are then introduced into the mixture at room temperature, together with NaHCO₃, to a pH close to 8. The separated organic phase is washed with water, dried and concentrated. This gives 9.75 g of oil, which is dissolved in 150 ml of acetone; 2.6 g of 66°Bé sulphuric acid are then introduced into this solution; the precipitate formed is isolated and dried to give 8 g of hemisulphate of the final product, which melts at about 190° C. [α]D/20=+53.3° (c=1, CH₃OH).

The reaction can be carried out at room temperature; the yield is identical when it is extended 4 days.

EXAMPLE 8

Dextrorotatorymethyl alpha-(4,5,6,7-tetrahydro-5-thieno[3,2-c]pyridyl)(2-chlorophenyl)acetate a) 20.5 g of methyl (+)-alpha-(2-thienylethylamino)(2-chlorophenyl)acetate in solution in 200 ml of methylene chloride are introduced over 25 minutes with stirring into 40 ml of a 30% (w/w) aqueous solution of formaldehyde. After 3 hours+ stirring, the organic phase is separated off, washed with water and dried, and the solvent is evaporated off. The residue is dissolved in 50 ml of methylene chloride and the solution is introduced at 60° C. into 100 ml of anhydrous dimethylformamide containing hydrochloric acid at 6N concentration. After 1 h 30 min at this temperature the solvents are removed by distillation under reduced pressure and the residue is dissolved in 200 ml of methylene chloride and 100 ml of water; sodium bicarbonate is added to release the base from its hydrochloride, the organic phase is separated off, dried and concentrated under reduced pressure. The hemisulphate of the required product is prepared in 150 ml of acetone by reaction with 4.9 g of concentrated (96%) sulphuric acid. 17 g of precipitate are thus obtained.

[α]D/20=+53° (c=1, CH₃OH).

We claim:

1. A process for the preparation of the dextrorotatory isomer of the compound of

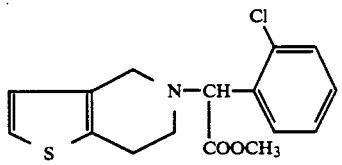

wherein a formylating agent chosen from formaldehyde, its hydrate or its polymer forms, the compound of formula XCH$_2$Y in which X is a halogen atom, a C$_1$–C$_4$ alkoxy group, a C$_1$–C$_4$ alkylthio group or an amino group, and Y is a C$_1$–C$_4$ alkoxy group, a C$_1$–C$_4$ alkylthio group, amino or a C$_2$–C$_5$ alkoxycarbonyl or phenoxycarbonyl group and a heterocyclic compound of formula

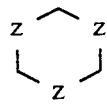

in which Z is O, NH or S is reacted with the dextrorotatory isomer of the compound of formula

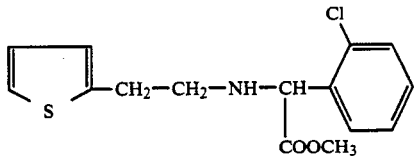

and the compound formed is cyclised in the presence of an acid.

2. The process according to claim 1, wherein the cyclisation is carried out in the presence of a strong inorganic acid and dimethylformamide.

3. The process according to claim 1, wherein said acid is formic acid and it is also used as a solvent for the reactions.

4. The process according to claim 1, wherein said acid is a strong acid introduced in the form of its salt with the compound II.

5. Racemic methyl alpha-(2-thienylethylamino)(2-chlorophenyl)acetate and its salts.

6. Dextrorotatory methyl alpha-(2-thienylethylamino) (2-chlorophenyl)acetate and its salts.

7. Laevorotatory methyl alpha-(2-thienylethylamino) (2-chlorophenyl)acetate and its salts.

* * * * *